United States Patent [19]

Johnson et al.

[11] Patent Number: 5,665,385
[45] Date of Patent: Sep. 9, 1997

[54] DIETARY METAL SUPPLEMENTS

[75] Inventors: Barry L. Johnson, Liberty, Utah; Al. F. Czap, Sandpoint, Id.

[73] Assignee: Sound Nutrition, Inc., Sandpoint, Id.

[21] Appl. No.: 353,539

[22] Filed: Dec. 9, 1994

[51] Int. Cl.⁶ .............................. A61K 9/48; A61K 9/16; A61K 9/26

[52] U.S. Cl. ................ 424/451; 424/400; 424/440; 424/465; 424/489

[58] Field of Search ........................ 424/400, 440, 424/451, 465, 489

[56] References Cited

U.S. PATENT DOCUMENTS

| | | | |
|---|---|---|---|
| 3,821,432 | 6/1974 | Mohammed | 426/167 |
| 4,315,927 | 2/1982 | Evans | 424/245 |
| 4,961,937 | 10/1990 | Rudel | 426/19 |
| 5,270,297 | 12/1993 | Paul et al. | |
| 5,292,538 | 3/1994 | Paul et al. | 426/74 |
| 5,300,657 | 4/1994 | Harirchian et al. | 549/420 |
| 5,480,970 | 1/1996 | Pollak et al. | |

OTHER PUBLICATIONS

Keller, J. R., *In Vivo Biopotency Evaluation of Chromium Containing Complexes*, Utah State University Masters Thesis, 1994, pp. 1–27, 67–94, 99–102.

*Primary Examiner*—Thurman K. Page
*Assistant Examiner*—M. Sikha
*Attorney, Agent, or Firm*—Seed and Berry LLP

[57] ABSTRACT

There are disclosed compositions and methods for supplementing dietary intake of various metals in a warm-blooded animal. The compositions include highly water soluble metal chelidamate salts and metal arginine salts in combination with a pharmaceutically acceptable carrier or diluent. The methods include the administration of such metal chelidamate or arginine salts to prevent or alleviate conditions resulting from metal deficiency.

26 Claims, No Drawings

DIETARY METAL SUPPLEMENTS

TECHNICAL FIELD

The present invention relates generally to compositions and methods for preventing or alleviating metal deficiencies in warm-blooded animals and, more specifically, to highly water soluble metal chelidamate and metal arginate complexes for use as dietary supplements.

BACKGROUND OF THE INVENTION

The assimilation of an adequate quantity of metals, including chromium, iron, selenium, molybdenum, vanadium, and boron, is essential for the health of warm-blooded animals. To overcome the adverse health risks associated with dietary deficiencies of these and other trace metals, dietary supplements have been formulated. The limitation of most of these metal-based formulations is their relatively low water solubility. Low solubility of these metal complexes in water results in their low absorption into the bloodstream of a warm-blooded animal. Low absorption of these metal complexes translates into inefficient administration and ultimately in ineffectiveness of delivery of these vital metals. Because of low metal complex solubility, administration of these poorly soluble metal complexes results in a limited availability of these metals to the warm-blooded animal.

The most readily available metal complexes are those complexes ligated with inorganic ligands such as chloride and oxide elemental metals. The solubility of these complexes is exceedingly low in aqueous systems. Organic complexes typically do not enhance water solubility. Because of their limited solubility, elemental metals, metal inorganic complexes, and most metal organic complexes are inefficient agents for the delivery of metals.

Accordingly, there is a need in the art for the development of new metal complexes for use as dietary supplements which are highly soluble in water and permit rapid absorption into the bloodstream of a warm-blooded animal to alleviate or prevent the adverse health consequences of particular metal deficiencies. The present invention fulfills these objectives, and provides further related advantages.

SUMMARY OF THE INVENTION

Briefly stated, the present invention discloses highly water soluble metal salt compositions for use as dietary supplements, as well as methods for supplementing metals in a warm-blooded animal by administering to the animal a therapeutically effective amount of a metal salt. More specifically, metal chelidamate salts and metal arginate salts are disclosed. In a preferred embodiment, the metal is either chromium, iron, manganese, selenium, molybdenum, vanadium, or boron and the salt is either a chloride or acetate salt. In one particularly preferred embodiment, the metal chelidamate salt is chromium chelidamate chloride. In another particularly preferred embodiment, the metal arginate salt is chromium arginate chloride.

The compositions of the present invention include metal chelidamate and metal arginate salts in combination with a pharmaceutically acceptable carrier or diluent. Such compositions are administered in a quantity sufficient to deliver an effective amount of a metal to the animal. These compositions may be orally administered in a variety of formulations, including in the form of an aqueous solution or in dry form, such as a powder, tablet, or capsule. Alternatively, the metal chelidamate and metal arginate salts may be administered in combination with a food material. In another aspect of the invention, a method of manufacturing the compositions of the present invention is disclosed.

Other aspects of this invention will become apparent upon reference to the attached figures and the following detailed description.

DETAILED DESCRIPTION OF THE INVENTION

The present invention is directed to metal salt compositions useful in preventing or alleviating conditions of deficiencies of certain metals in warm-blooded animals, as well as methods relating to the administration thereof. The metal salt compositions of the present invention are highly water soluble and include metal chelidamate salts and metal arginate salts. The metal chelidamate and metal arginate salts may be formulated for administration to a warm-blooded animal by combination with a pharmaceutically acceptable carrier or diluent. Such compositions are administered in a quantity sufficient to deliver an effective amount of a metal to the animal. A preferred method of administration is oral delivery of the composition, and the composition is preferably formulated in a manner suitable for oral administration.

The metal complexes of the present invention are metal salts in general, and more specifically, metal chelate salts. As such, these metal salts comprise a metal chelated by a ligand and also include a counterion. Accordingly, as used herein, the term "metal chelidamate salt" refers to a metal chelated by a chelidamic acid ligand and includes a counterion such as chloride or acetate. Similarly, as used herein, the term "metal arginate salt" refers to a metal chelated by an arginine ligand and includes a counterion such as chloride or acetate.

In the practice of the present invention, a variety of metal species may be effectively delivered by the metal chelidamate and metal arginate salts of the present invention. The metal salts of the present invention include metal which may be classified as either minerals or trace minerals, and include metals such as chromium, iron, manganese, selenium, molybdenum, vanadium, zinc, copper, and boron among others. The oxidation states of the metals of the metal salts of the present invention is variable and dependent upon the particular metal of the metal salt. For example, suitable metals of specific oxidation state include chromium (II), chromium (III), chromium (IV), iron (II), iron (III), manganese (II), manganese (III), selenium (IV), molybdenum (IV), molybdenum (VI), vanadium (III), vanadium (IV), vanadium (V), zinc (II), copper (I), copper (II), and boron (III). Preferred metals of specific oxidation state include chromium (III), iron (III), manganese (III), molybdenum (VI), vanadium (V), zinc (II), and copper (II). In a preferred embodiment, the metal chelidamate and metal arginate salts are chromium (III) chelidamate and chromium (III) arginate salts.

As mentioned above, the metal salts of the present invention include counterions in addition to the metal and chelated chelidamic acid or chelated arginine. Suitable counterions include chloride and acetate counterions. In a preferred embodiment, the counterion is chloride.

The metal salts of the present invention are prepared by treatment of a metal complex such as chromium chloride or chromium acetate with either chelidamic acid or arginine. All of these reagents are available from a variety of commercial sources (e.g., Aldrich Chemical Company, Milwaukee, Wis.). For example, combination of chromium chloride and chelidamic acid, each in a minimum amount of hot distilled water followed by adjustment of the pH to 4.5 with ammonium hydroxide results in the formation of chromium chelidamate chloride. Similar treatment of chromium acetate with chelidamic acid provides chromium chelidamate acetate.

In an analogous procedure, reaction of arginine with chromium chloride or chromium acetate yields chromium arginine chloride and chromium arginine acetate, respectively. While these procedures exemplify the formation of chromium chelidamate and chromium arginine salts, one skilled in the art would recognize that these procedures are representative of other metal chelidamate and arginate salt preparations of this invention.

The metal chelidamate and metal arginine salts prepared as described above have surprisingly high water solubility. For example, chromium chelidamate chloride is soluble in water to the extent of 0.51 g/100 mL (at 20° C.) and 0.90 g/100 mL (at 40° C.); and chromium arginate chloride is soluble in water to the extent of 2.39 g/100 mL (at 20° C.) and 4.48 g/100 mL (at 40° C.). The solubility of these compounds prepared as described above is significantly greater than for the non-salt form of the complexes. Specifically, the solubility of the salt form of the chromium chelidamate complex is about 5 times that of the non-salt form at 20° C. and about 7 times that of the non-salt form at 40° C. For the chromium arginate complexes, the salt form is more than 2 times as soluble as the non-salt form at 20° C. and about 2.5 times as soluble as the non-salt form at 40° C. Accordingly, the use of these highly water soluble metal salts is particularly advantageous in dietary supplement formulations.

The compositions of the present invention include a metal chelidamate salt and/or a metal arginate salt and may be formulated by combination with a pharmaceutically acceptable carrier or diluent to facilitate administration. The diluent or carrier should not interact with the metal chelidamate or metal arginate salt to significantly reduce the effectiveness thereof. The preparations may be manufactured into compressed tablets, capsules or a powder using a variety of known techniques. Methods for encapsulating compositions (such as in a coating of hard gelatin) for oral administration are well known in the art (Baker, Richard, *Controlled Release of Biological Active Agents*, John Wiley and Sons, 1986) (incorporated herein by reference). The powder or tablet forms of the preparation may be dissolved in water or other drinks for oral administration as an aqueous solution. Alternatively, the powder or tablet forms of the preparation may be combined in solid foods.

In another embodiment of the invention, a method for supplementing a metal in a warm-blooded animal diet is disclosed. The method for supplementing a metal in the diet of a warm-blooded animal includes administering to the animal an effective amount of the metal chelidamate salt. Another embodiment of this invention discloses a method for supplementing a metal in the diet of a warm-blooded animal by administering an effective amount of a metal arginate salt. These methods may be effective prophylactically in preventing deficiencies in various metals and avoiding the conditions which result from particular metal deficiencies. Alternatively, these methods may be used therapeutically to alleviate the symptoms associated with metal deficiencies.

For dietary supplementation, oral administration levels vary according to the particular metal. For example, oral maintenance levels of chromium typically range from 10 to 150 ug elemental chromium per day. Such a level is comparable to a daily intake of about 20 to 500 ug elemental chromium per day. Therapeutic dosages may increased to 1,000 ug per day or higher, depending upon the severity of the deficiency. For the purposes of this invention, any dosage that will raise the level of a metal in a warm-blooded animal to a level within a normal range for the particular species, or alleviate the symptoms of the metal deficiency in the warm-blooded animal, is considered an effective amount or effective dose.

The compositions of the present invention may be formulated by admixing either a metal chelidamate salt or a metal arginate salt with a pharmaceutically acceptable carrier or diluent by techniques known to those skilled in the formulation field.

From the foregoing, it will be appreciated that, although specific embodiments of this invention have been described herein for the purposes of illustration, various modifications may be made without deviating from the spirit and scope of the invention. Accordingly, the invention is not limited except by the appended claims.

We claim:

1. A composition for supplementing a metal in the diet of a warm-blooded animal, comprising a metal chelidamate salt and a pharmaceutically acceptable carrier or diluent.

2. The composition of claim 1 wherein the metal of the metal chelidamate salt is selected from the group consisting of chromium, iron, manganese, selenium, molybdenum, vanadium and boron.

3. The composition of claim 1 wherein the metal chelidamate salt is selected from the group consisting of metal chelidamate chloride and metal chelidamate acetate.

4. The composition of claim 1 wherein the metal chelidamate salt is chromium chelidamate chloride.

5. A method for supplementing a metal in the diet of a warm-blooded animal, comprising administering to the animal a metal chelidamate salt.

6. The method of claim 5 wherein the metal of the metal chelidamate salt is selected from the group consisting of chromium, iron, manganese, selenium, molybdenum, vanadium and boron.

7. The method of claim 5 wherein the metal chelidamate salt is selected from the group consisting of metal chelidamate chloride salt and metal chelidamate acetate salt.

8. The method of claim 5 wherein the metal chelidamate salt is chromium chelidamate chloride.

9. The method of claim 5 wherein the metal chelidamate salt is administered orally.

10. The method of claim 5 wherein the metal chelidamate salt is administered as an aqueous solution.

11. The method of claim 5 wherein metal chelidamate salt is administered as a tablet, capsule or powder.

12. The method of claim 5 wherein the metal chelidamate salt is administered in combination with a food material.

13. A process for manufacturing a composition for supplementing a metal in the diet of a warm-blooded animal, comprising admixing a metal chelidamate salt with a pharmaceutically acceptable carrier or diluent.

14. A composition for supplementing a metal in the diet of a warm-blooded animal, comprising a metal arginate salt and a pharmaceutically acceptable carrier or diluent.

15. The composition of claim 14 wherein the metal of the metal arginate salt is selected from the group consisting of chromium, iron, manganese, selenium, molybdenum, vanadium and boron.

16. The composition of claim 14 wherein the metal arginate salt is selected from the group consisting of metal arginate chloride and metal arginate acetate.

17. The composition of claim 14 wherein the metal arginate salt is chromium arginate chloride.

18. A method for supplementing a metal in the diet of a warm-blooded animal, comprising administering to the animal a metal arginate salt.

19. The method of claim 18 wherein the metal of the metal arginate salt is selected from the group consisting of chromium, iron, manganese, selenium, molybdenum, vanadium and boron.

20. The method of claim 19 wherein the metal arginate salt is selected from the group consisting of metal arginate chloride and metal arginate acetate.

21. The method of claim 19 wherein the metal arginate salt is chromium arginate chloride.

22. The method of claim 19 wherein the metal arginate salt is administered orally.

23. The method of claim 19 wherein the metal arginate salt is administered as an aqueous solution.

24. The method of claim 19 wherein metal arginate salt is administered as a tablet, capsule or powder.

25. The method of claim 19 wherein the metal arginate salt is administered in combination with a food material.

26. A process for manufacturing a composition for supplementing a metal in the diet of a warm-blooded animal, comprising admixing a metal arginate salt with a pharmaceutically acceptable carrier or diluent.

\* \* \* \* \*

UNITED STATES PATENT AND TRADEMARK OFFICE
CERTIFICATE OF CORRECTION

PATENT NO.    : 5,665,385
DATED         : September 9, 1997
INVENTORS     : Barry L. Johnson and Al F. Czap It is certified that errors appear in the above identified patent and that said Letters Patent is hereby corrected as shown below:

Claims 14-26 were cancelled during prosecution and therefore improperly issued.

Signed and Sealed this

Seventh Day of April, 1998

*Attest:*

BRUCE LEHMAN

*Attesting Officer*     *Commissioner of Patents and Trademarks*